United States Patent [19]

Pettit et al.

[11] Patent Number: 4,873,245
[45] Date of Patent: Oct. 10, 1989

[54] ISOLATION AND STRUCTURAL ELUCIDATION OF CEPHALOSTATINS 1-4

[75] Inventors: George R. Pettit, Paradise Valley; Yoshiaki Kamano, Tempe, both of Ariz.

[73] Assignee: Arizona Board of Regents, Tempe, Ariz.

[21] Appl. No.: 167,550

[22] Filed: Mar. 14, 1988

[51] Int. Cl.$^4$ .................. C07D 491/22; A61K 31/495
[52] U.S. Cl. ...................................... 514/250; 544/230
[58] Field of Search ................. 544/338, 230; 514/250

[56] References Cited
PUBLICATIONS

Pettit, Chem Abs 108, 128802d (1988).

*Primary Examiner*—Mark L. Berch
*Attorney, Agent, or Firm*—Richard R. Mybeck

[57] ABSTRACT

The marine worm *Cephalodiscus gilchristi* (Hemichordata phylum) from Southeast Africa has been found to contain powerful inhibitors of the murine P388 lymphocytic leukemia, herein denominated "cephalostatin 1, cephalostatin 2, cephalostatin 3 and cephalostatin 4". Pharmaceutical preparations containing the substances and methods of use are described. Cephalostatin 1-3 having the following structure:

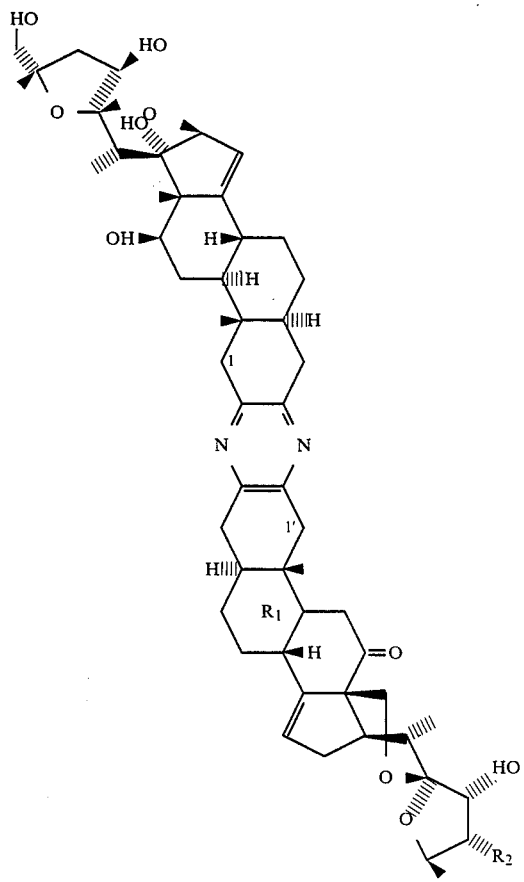

1: $R_1 = H, R_2 = H$
2: $R_1 = OH, R_2 = H$
3: $R_1 = OH, R_2 = CH_3$ (Abstract continued on next page.)

whereas cephalostatin 4 is an oxy- derivative of cephalostatin 2, having oxygen interposed in the 14-15 double bond as shown below:

24 Claims, 3 Drawing Sheets

SEPARATION SCHEME Part 1

FIG. 1

SEPARATION SCHEME Part 2

FIG. 2

SEPARATION SCHEME Part 3
FIG. 3

ISOLATION AND STRUCTURAL ELUCIDATION OF CEPHALOSTATINS 1-4

INTRODUCTION

The present invention relates to the isolation and structural elicidation of new substances of marine origin herein denominated "Cephalostatins". The Cephalostatins have been found to be powerful inhibitors of the murine P388 lymphocytic leukemia.

Financial assistance for this project was provided by the Arizona Disease Control Research Commission and DHHS Grants CA-16049-05-11 and NO1-CM-97262.

BACKGROUND OF THE INVENTION

The invertebrate chordates have some vertebrate characteristics such as a dorsal tubular nervous system and notochord. Among such phyla lacking a vertebral column occurs the Hemichordata. The class Pterobranchia of this phylum has not previously been explored with respect to biologically active or other chemical constituents.

In late 1972, we collected by SCUBA (ca. 20 m) in the Indian Ocean Off Southeast Africa, in areas patrolled by the great white shark *Carchorodon carchoris*, specimens from this class of the marine worm (~5 mm long in tube colonies) *Cephalodiscus gilchristi* (order cephalodiscida). Two years later, methanol and water extracts of *C. gilchristi* demonstrated a confirmed active level against the U.S. National Cancer Institute's murine P388 lymphocytic leukemia (PS system) and obtained a 32-41% life extension at 25-37.5 mg/kg. Now after more than fifteen years of relentless research directed at discovering the active constituent(s) of *C. gilchristi*, we have succeeded in the isolation and structural elucidation of a series of powerful cell growth inhibitory substances with PS cell line $ED_{50}$ of $10^{-7}$ to $10^{-9}$ μg/ml. We have denominated these substances as "cephalostatin 1", "cephalostatin 2", "cephalostatin 3", and "cephalostatin 4".

BRIEF SUMMARY OF THE INVENTION

Four new substances have been isolated from *Cephalodiscus gilchristi*, structurally elucidated, and found to have a confirmed active level against the U.S. National Cancer Institute's murine P388 lymphocytic leukemia (PS system). These substances are herein denominated "cephalostatin 1", "cephalostatin 2", "cephalostatin 3", and "cephalostatin 4". Cephalostatins 1-3 have the following structure:

1: $R_1 = H$, $R_2 = H$

2: $R_1 = OH$, $R_2 = H$

3: $R_1 = OH$, $R_2 = CH_3$

Whereas cephalostatin 4 is an oxy derivative of cephalostatin 2 having oxygen interposed in the 14-15 double bond in the structure as shown below.

DESCRIPTION OF PREFERRED EMBODIMENTS

Several attempts to isolate the substance herein denominated "cephalostatin 1" were made with recollections of *C. gilchristi* until the problem was eventually solved using 166 kg wet wt, including Coenecium. A methylene chloride-methanol extract was successively partitioned using the system 9:1→4:1→3:2 methanol-water against hexane→carbon tetrachloride→methanol. The active methylene chloride fraction (28 g) was separated using a detailed bioassay (PS) guided series of gel permeation, partition (SEPHADEX® LH20 and LH60, silica gel, e.g., with 10:10:1 hexane-ethyl acetate-methanol to 10:10:1 hexane-methylene chloride-methanol) gradient column chromatograms, to HPLC on PARTISIL® M9 employing methanol-water gradients. Cephalostatin 1 was obtained in $8.36 \times 10^{-4}\%$ yield: 138.8 mg as needles from ethyl acetate-methanol; mp 326° C. (dec); $R_f$ 0.35 (SiO$_2$ plate, 90:10:0.8 methylene chloride-methanol-water; $[\alpha]_D^2 + 102$ (c=0.04, CH$_3$OH); SP-HRSIMS[3] 911.5424 ([M+H]$^+$ for C$_{54}$H$_{74}$N$_2$O$_{10}$, calcd. 911.5423); UV (CH$_3$CH$_2$OH)$\lambda_{max}$ 289 ($\epsilon$ 15,233) and 309 (shoulder) nm; IR (KBr): 3430, 3050, 2970, 2930, 2880, 2860, 1708, 1650-1615 (br), 1455, 1400, 1152, 1115, 1090, 1045, 950, and 892 cm$^{-1}$. See Tables I and II for $^{13}$C- and H-NMR assignments. The chemical shifts were rigorously assigned by using results of HH-, HC-, and HH- relayed COSY, COLOC, HHC- RELAY, and NOE experiments.

TABLE I

100 MHz $^{13}$C—NMR (deuteriopyridine): 9.01 (C-21), 11.31 (C-19') 11.72 (C-19), 12.58 (C-18), 15.49 (C-21'), 26.42 (C-27), 27.94 (C-6), 28.23 (C-6'), 28.69 (C-7), 28.94 (C-11), 29.44 and 29.75 (C-26' and C-27'), 29.50 (C-7'), 32.36 (C-16'), 32.88 (C-20'), 33.79 (C-8), 35.56 (C-8'), 35.72 (C-4), 35.78 (C-4'), 36.28 (C-10'), 36.32 (C-10), 38.81 (C-11'), 39.51 (C-24), 41.20 (C-5'), 41.78 (C-5), 44.21 (C-17'), 44.50 (C-20), 45.82 (C-1'), 45.98 (C-1), 47.32 (C-24'), 52.20 (C-9'), 53.20 (C-9), 55.39 (C-13), 61.82 (C-13'), 64.19 (C-18'), 69.28 (C-26), 71.51 (C-23), 75.59 (C-12), 81.12 (C-25'), 81.52 (C-23'), 82.81 (C-25), 91.66 (C-17), 93.15 (C-16), 110.96 (C-22'), 117.16 (C-22), 122.28 (C-15), 123.18 (C-15'), 148.38, 148.44, 148.66, 149.01 and 149.46 (C-2, C-3, C-2', C-3', and C-14'), 152.71 (C-14), and 211.80 (C-12') ppm.

TABLE II

400 MHz $^1$H—NMR (deuteriopyridine): 0.72 (3H, s, H-19'), 0.75 (3H, s, H-19), 0.88 (dt, 4.5, 13.8, H-9), 1.26 (m, H-9'), 1.28 (m, H-6b'), 1.30 (m, H-7b'), 1.33 (3H, s, H-18), 1.34 (m, H-6b), 1.35 (m, H-7b), 1.35 (3H, d, 7.0, H-21), 1.39 (3H, s, H-27'), 1.47 (3H, d, 7.0, H-21'), 1.47 (3H, s, H-26'), 1.53 (m, H-6a'), 1.59 (m, H-6a'), 1.60 (m, H-5'), 1.61 (m, H-5), 1.65 (3H, s, H-27), 1.69 (m, H-7a), 1.77 (dt, 10.0, 14.0, H-11b), 1.95 (dd, 6.2, 12.0, H-24b'), 1.99 (m, H-7a'), 2.04 (m, H-11a), 2.07 (m, H-8), 2.13 (m, H-8'), 2.33 (m, H-16b')2.35 (m, H-24a'), 2.36 (m, H-24b), 2.56 (d, 17.0, H-1b'), 2.61 (dd, 14.0, 3.2, H-11b'), 2.64 (d, 17.0, H-1b), 2.65 (2H, dd, 18.0, 12.5, H-4b and H-4b'), 2.72 (dd, 12.0, 7.0, H-17'), 2.77 (dd, 10.5, 7.9, H-24a), 2.78 (t, 14.0, H-11a'), 2.86 (q, 7.0, H-20), 2.87 (dt, 4.0, 11.8, H-16a'), 2.91 (dd, 17.9, 5.5, H-4a') 2.93 (dd, 17.9, 5.5, H-4a), 3.04 (d, 17.0. H-1a'), 3.07 (d, 17.0, H-1a), 3.17 (dq, 7.0, 7.0, H-20'), 3.72 (d, 11.2, H-26a), 3.78 (d, 11.2, H-26b), 4.02 (d, 12.2, H-18a'), 4.05 (m, H-12), 4.06 (d, 12.2, H-18b'), 4.70 (s, C-12 OH), 4.80 (2H, m, H-23 and H-23'), 5.24 (s, H-16), 5.44 (s, H-15'), 5.64 (s, H-15), 6.23 (s, C-17 OH), 6.54 (br s, C-26 OH) 7.19 (br, s, C-23' OH) and 8.06 (br s, C-23 OH) ppm.

Cephalostatin 1 gave a tetraacetate derivative: SP-HRSIMS m/e 1079.5798 [M+H]$^+$ for C$_{62}$H$_{82}$N$_2$O$_{14}$. But SP-SIMS active hydrogen determination by hydrogen-deuterium exchange indicated five such hydrogen atoms. The yellow-orange reaction to Dragendorf's reagent and positive response to 12-molybdophosphoric acid suggested a steroidal alkaloid-type structure. However, the structural problem proved refractory to complete solution by high field NMR and mass spectral techniques and required crystal structure determination. As cephalostatin persisted in crystallizing in long fibrous needles, preparation of suitable crystals for x-ray proved to be especially difficult and was only solved when this remarkable substance was found to form a useful solvate with pyridine that slowly crystallized (as small plates) at ambient temperature from pyridine-hexane.

On the basis of Laue' symmetry and systematic extinctions, the crystal chosen (0.5×0.2×0.1 mm) was assigned the orthorhombic space group P2$_1$2$_1$2$_1$: a=14.863, b=14.992, c=26.354 Å, as calculated from a least-squares fit of 25 diffractometer measured 2θ reflections. A measured density of 1.197 g/cc and mass spectral data indicated one molecule of cephalostatin 1 and two molecules of pyridine per asymmetric unit. Although it became immediately apparent that a deficiency in the number of measurable reflections at room temperature existed (<40%), attempts at low temperature collections were abandoned due to an apparent space group transition over a wide range of reduced temperatures. Consequently, all unique reflections with $20° < 130°$ were measured at room temperature using a graphite-monochromated Cu K radiation (1.54178 A) and a −20 scan technique. A total of 8825 (one hemisphere) reflections were collected and corrected for Lorentz, polarization and absorption effects; the latter involving an empirical correction based on orientation and psi scans. Of the reflections collected, only 3380 (38%) were judged observed, $\}[Fo] \geqq 3 [Fo]\}$.

Structure solution was accomplished by means of direct methods with MULTAN-80. (See: Main, P. "A System of Computer Programs for the Automatic Solution of Crystal Structures from X-Ray Diffraction Data," University of York, England, 1980.) An adequate phasing model was obtained from the trial sets generated by the multisolution tangent formula: the one exhibiting the best figure of merit being used in subsequent Karle recycling techniques as described in Karle, I. L., Acta Crystallogr., Sect. B 1968, B 24, 182–186. (b) Karle, I. L., "Crystallographic Computing Techniques." Ahmed, F. R., Ed., Munksgaard, Copenhagen, 1976, pp 186–193 and references therein. The location of oxygen and nitrogen atoms of cephalostatin 1 was deduced by occupancy refinement methods, as well as bond lengths and NMR spectral data. The pyridine ring atoms were constrained to 1.028 C atom equivalents for refinement purposes. The nonhydrogen atom model converged to $R=0.121$, $Rw=0.103$. Atomic coordinates for all H atoms attached to carbon were calculated at idealized positions. The full matrix least-squares isotropic refinement of the total asymmetric contents (H atom coordinates and thermal parameters fixed) converged to a residual of $R=0.089$, $Rw=0.058$ (anomalous dispersion corrections made using 3380 reflections).

Computer generated perspective views of cephalostatin 1 were obtained and, based upon the absolute stereochemical configuration of the well established steroid nucleus, the stereochemical assignments at the remaining eleven asymmetric carbon atoms are: 12R, 16S, 17S, 20S, 22S, 23R, 25S, 17'R, 20'S, 22'R, 23'R.

The structure of cephalostatin 1 is quite unique, consisting of 9 fused rings formed by the coupling of two steroid nucleii at C2 and C3. In addition, two spiroketal rings terminate each end of the fused ring system generating a total of 13 rings. A very slight bend in the nearly planar fused ring array is apparent when the molecule is viewed edgewise, as shown above. The overall dimensions of cephalostatin 1 are approximately 30 Å long, 9 Å wide and 5 Å thick. The bond angles and distances are within generally accepted limits. The thermal parameters of several atoms were consistently large, i.e., isotropic $U=0.09-0.13$, for the carbonyl oxygen $O_{12}'$, and the substituents at opposing ends of the molecule- $O_{26}$, $C_{26}'$ and $C_{27}'$. In addition, the temperature factors for the atoms of both pyridine solvent molecules were quite large. A more detailed crystallographic analysis is shown in the examples.

It is surmised that cephalostatin 1 results in part from a biosynthetic condensation of 2-amino-3-oxo steroid units to yield a powerful inhibitior of cell growth that may in turn serve in the chemical defense and/or in other important functions of *C. gilchristi*.

Cephalostatin 2 recrystallized from ethyl acetate-methanol as needles (242.8 mg, $14.6 \times 10^{-4}\%$ yield): m.p. >350° C.; $R_f(SiO_2)$ 0.28 (90:10:0.8 methylene chloride-methanol-water); $[\alpha]_D$ +111 (c=0.07, $CH_3OH$); SP-HRSIMS: (6, glycerol−$CF_3SO_3H$) 927.5230 $(M+H)^+$ for $C_{54}H_{75}N_2O_{11}$, calcd. 927.5372; UV (EtOH): 290 (13,700), 308 (sh) nm; IR (KBr): 3430, 3055, 2975, 2930, 2880, 1710, 1655–1625 (br), 1448, 1402, 1385, 1092, 1045, and 950 $cm^{-1}$. Cephalostatin 3 also recrystallized as needles (21.2 mg, $1.2 \times 10^{-4}\%$ yield) from ethyl acetate-methanol: m.p. >350° C.; $R_f(SiO_2)$ 0.30 (cf. conditions); $[\alpha]_D$+99° (c=0.15, CH OH; SP-HRSIMS: (glycerol−$CF_3SO_3H$) 941.5546 $(M+H)+$for $C_{55}H_{77}N_2O_{11}$, calcd. 941.5528; UV (EtOH): 290 (12,900), 308 (sh) nm; IR (KBr): 3430, 3050, 2967, 2928, 2872, 1707, 1645–1615 (br), 1446, 1383, 1040, 977, 952, and 935 $cm^{-1}$. Cephalostatin 4 was isolated as a colorless solid (8.0 mg, $4.5 \times 10^{-5}\%$ yield): m.p. >350° C.; $[\alpha]_D$+89° (c=0.11, $CH_3OH$); SP-HRSIMS: (glycerol−$CF_3SO_3H$) 943.5309 $(M+H)^+$ for $C_{54}H_{75}N_2O_{12}$, calcd. 943.5243; UV (EtOH): 290 (10,500), 308 (sh) nm; IR (KBr): 3430, 2970, 2928, 2875, 1711, 1660–1600 (br), 1447, 1383, 1089, 1042, 948, and 904 $cm^{-1}$. With the X-ray crystal structure assigned cephalostatin 1 as a reference point, it became possible using detailed analysis of the high field $^1H$- and $-^{C-nmr}$ spectra, the mass spectra, and results of elemental analyses, to unequivocally assign structures 2, 3, and 4 respectively to cephalostatins 2, 3, and 4.

Both cephalostatins 2 and 3 contain one additional active hydrogen compared to cephalostatin 1, as evidenced by SP-SIMS hydrogen-deuterium exchange. However, both substances gave only tetraacetate derivatives as experienced with cephalostatin 1. Cephalostatin 2 displayed $^1H$- and $^{13}C$- nmr spectra very similar to those of cephalostatin 1. Cephalostatin 2 was found to possess (by mass analyses) one more oxygen atom than cephalostatin 1. Evidence for this additional oxygen atom was also observed in the $^{13}C$-nmr spectrum with the appearance of a quaternary carbon at 78.74 ppm and the disappearance of the C-9' methine carbon at 52.20 ppm. The rest of the spectrum remained essentially unchanged. This is indicative of an hydroxyl group at C-9' as shown above.

The $^1H$- and $^{13}C$- nmr spectra of cephalostatins 2 and 3 proved to be almost identical, except for the signals assigned to C-22' to C-27'. An additional methyl group, in cephalostatin 3, was evidenced by a new 3 hydrogen methyl doublet at 1.10 ppm and by its molecular formula. The C-23' methine became a doublet of 11.4 Hz and showed a correlation peak to the new methyl doublet in a homonuclear relayed coherence transfer experiment (RELAY). Thus a methyl group was found attached to C-24'.

The $^1H$- and $^{13}C$- nmr spectra of cephalostatin 4 proved to be very similar to those of cephalostatin 2, except for the absence of signals attributed to the 14'-15' double bond. The mass spectrum indicated the presence of an additional oxygen atom. By following the coupling network from C-21' (methyl doublet at 1.30 ppm) using COSY and RELAY experiments, it was determined that C-15' shares an epoxy group with C-14', as shown above.

The thirteen fused or otherwise connected rings of the Cephalostatins may constitute the largest of such naturally occurring marine animal systems presently known. The isolation and structural elucidation of Cephalostatins 2, 3 and 4 will now allow an initial assessment of structure activity relationships among this remarkable new series of vigorous cell growth inhibitors. Antineoplastic and other biological evaluations are in progress.

To further aid in the understanding of the present invention, and not by way of limitation, the following examples are presented.

EXAMPLE I

General Methods

All solvents employed for chromatographic purposes were redistilled. Column chromatography was performed using either SEPHADEX® LH-60, from Pharmacia Fine Chemicals, AB, Uppsala, Sweden, or silica gel (70–230 mesh) from E. Merck, Darmstadt. The HPLC columns (9.4×500 mm) employed were the Partisil-10 M-9-ODS-2 (C-18 reversed phase) and Partisil-10 M-9 columns from Whatman, Inc., Clifton, N.J. An Altex HPLC unit with System Controller Model 420 and Model 110A pumps was utilized for final separations. Silica gel GF Uniplates were supplied by Analtech, Inc., Newark, Del. All TLC plates were developed by UV light and (or) detected by anisaldehyde-acetic acid-sulfuric acid spray (plates heated to about 150° C. for 5 to 10 min). Fractions were collected with either Gilson FC-80 (microfractionator) or FC-220 (racet rack fractionator) equipment in conjunction with a Gilson UV monitor Model HM.

All melting points are uncorrected and were observed with a Kofler-type melting point apparatus. Ultraviolet spectra (methanol solution) were recorded with a Hewlett-Packard 8450A UV/VIS spectrometer. Optical rotations (methanol solution) were observed using a Perkin-Elmer Model 214 polarimeter. Mass spectra were determined with a MAT-312 mass spectrometer. Infrared spectra (KBr) were obtained with a Nicolet FTIR Model MX-1 spectrometer. The NMR spectra were measured with a Bruker WH-400 instrument, and deuteriopyridine was employed as solvent with tetramethylsilane as internal standard.

EXAMPLE II

Animal collection and preliminary experiments

In 1972, *Cephalodiscus gilchristi* (Chordata phylum, Hemichordata subphylum, Petrobaranchia class) was collected in False Bay, Cape Province, Republic of South Africa. All subsequent recollections were also from the same general area.

The initial sample of *Cephalodiscus gilchristi* was preserved in aqueous ethanol. Removal of solvent gave an extract that reached a confirmed level of activity against the National Cancer Institute's murine P388 lymphocytic leukemia (PS system) with a response of T/C 141 at 25 mg/kg.

EXAMPLE III

Animal extractions

The aqueous 2-propanol extract of the 1975 recollection was concentrated and partitioned between $CH_2Cl_2$ and water. The residual animal was extracted with 1:1 $CH_2Cl_2$-MeOH. Sufficient water was added to create two phases and the $CH_2Cl_2$ layer was separated and concentrated. The extraction procedure was repeated by adding sufficient MeOH to the MeOH-water and animal mixture to form a single phase. Again water was added to separate the $CH_2Cl_2$ which was collected and concentrated.

EXAMPLE IV

Solvent partition sequence

The $CH_2Cl_2$ extract was dissolved in 9:1 MeOH-water and extracted with hexane. The MeOH-water phase was diluted to 4:1 MeOH-water and extracted with $CCl_4$. The MeOH-water phase was diluted to 3:2 and extracted with $CH_2Cl_2$. The resulting hexane (1.33 g), $CCl_4$ (42 g), $CH_2Cl_2$ (28 g), and MeOH-water (62 g) fractions were concentrated and aliquots submitted for bioassay. Antineoplastic activity (PS in vitro $ED_{50}$ $4.5\times10^{-2}$ and $<1.0\times10^{-2}$) resided in the $CCl_4$ and $CH_2Cl_2$ fractions, respectively.

EXAMPLE V

Isolation of the cephalostatins

Figure 1:
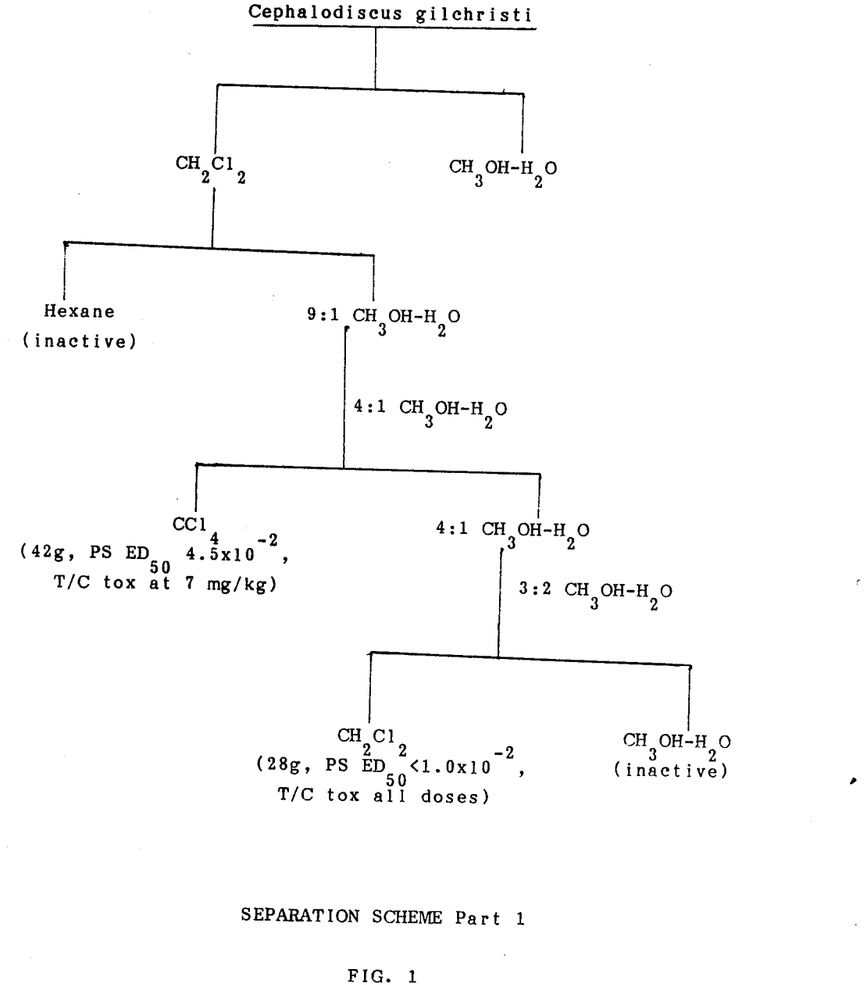
FIG. 1 is a flow diagram of the separation scheme part 1.
Figure 2:
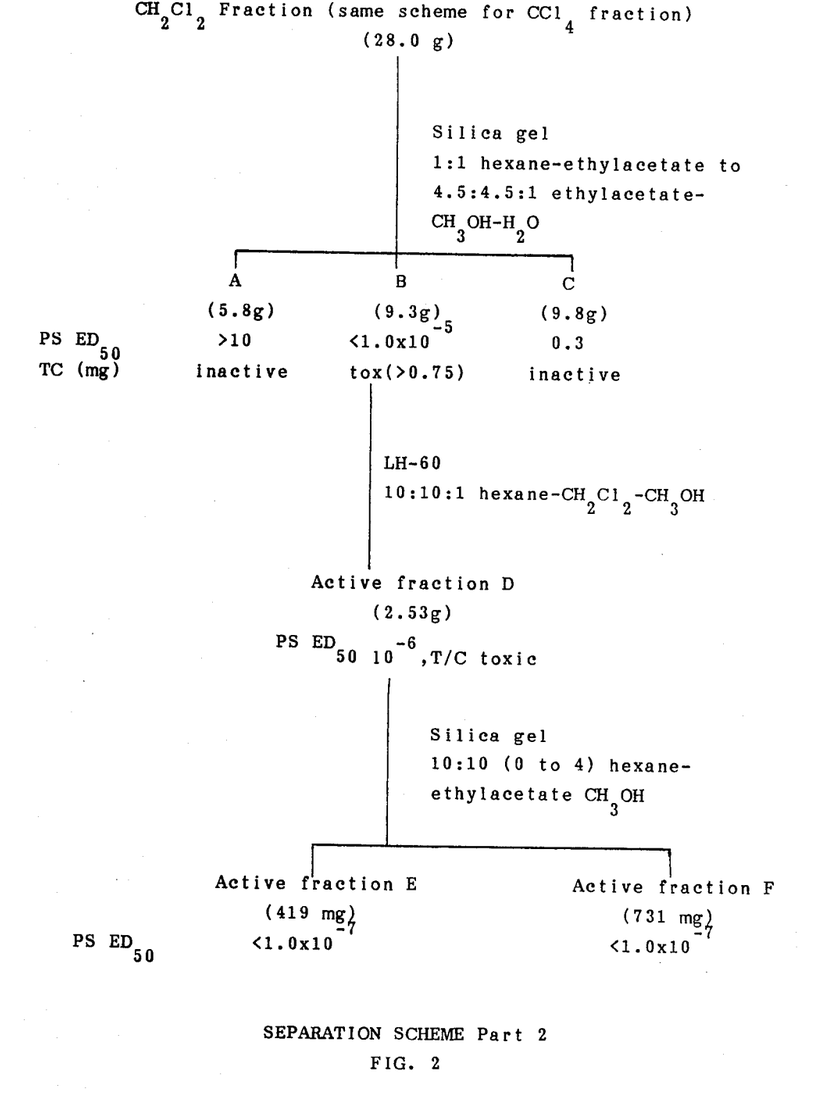
FIG. 2 is a flow diagram of the separation scheme part 2.
Figure 3:
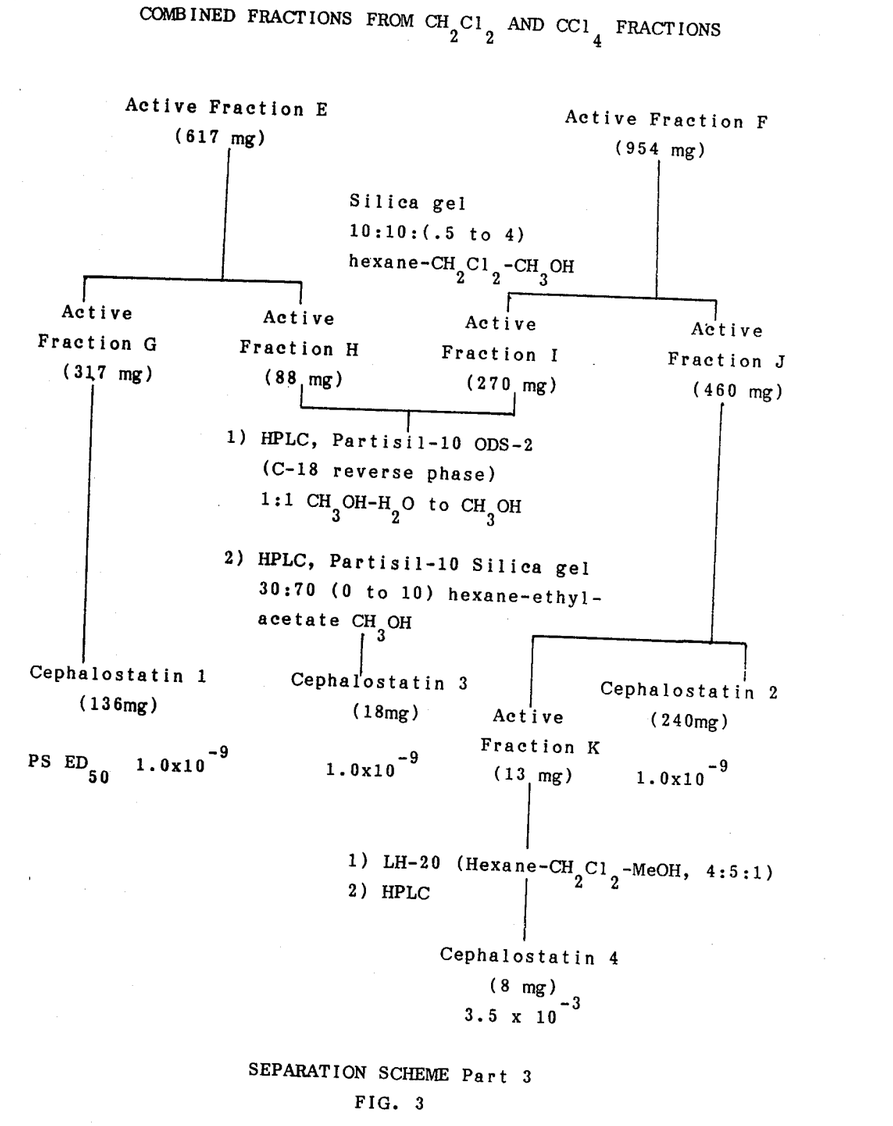
FIG. 3 is a flow diagram of the separation scheme part 3.

In a typical series of experiments the $CCl_4$ and $CH_2Cl_2$ active fractions as shown in FIG. 1 were chromatographed on a column of silica gel using a gradient elution from hexane-EtOAc to EtOAc-MeOH-water. The procedure was repeated until the total fractions were separated by this procedure. The principal in vitro active fraction B was further separated by a gel permeation procedure using SEPHADEX® LH-60 and 10:10:1 hexane-$CH_2Cl_2$-MeOH. Recombination of fractions on the basis of TLC properties, led to the principal in vitro active fraction D. Fraction D (2.53 g) was next separated by silica gel chromatography using gradient elution hexane-EtOAc-MeOH (10:10:0 to 4). By means of 12 ml fractions, 4000 ml was collected and of these, fractions noted as E and F in FIG. 2 were found to give the highest level of antineoplastic activity. At this point, active fractions E and F from the $CH_2Cl_2$ extract were combined with the corresponding ones from the $CCl_4$ extract as shown in FIG. 3. Extensive separation of the most active fractions E and F by further silica gel column chromatography using gradient elution (hexane-$CH_2Cl_2$-MeOH 10:10:0.5 to 4.0) in 7 ml fractions (500 ml total) afforded four active fractions G, H, I, and J. Fractions H and I were combined on the basis of TLC properties.

Fractions G to J were still quite complex and required extensive HPLC methods of separation. A solution of fraction G in 1:1 MeOH-water was chromatographed using HPLC techniques with a C-18 reverse phase column and a flow rate of 2.0 ml/min with a gradient to methanol. The fraction with the most promising PS activity was further separated by HPLC using a silica gel column and hexane-EtOAc-MeOH gradient (30:70:0 to 10) as mobile phase with a flow rate of 2.0 ml/min. By this means 136 mg of cephalostatin 1 was isolated. Fractions H, I and J were further separated in a procedure analogous to that used for fraction G, to yield cephalostatin 3 (18 mg), cephalostatin 2 (240 mg) and active fraction K (13 mg). Fraction K was further purified by SEPHADEX LH-20 using hexane—$CH_2C$-$H_2$—MeOH 4:5:1 and HPLC to yield cephalostatin 4 (8 mg).

EXAMPLE VI

Cephalostatin 1

The fraction designated Cephalostatin 1 was analyzed with the following results: UV (EtOH) 203 and 205 (12,500), 289 (15,233), 309 (sh); IR (KBr) 3430, 3050, 2970, 2930, 2880, 2860, 1708, 1650–1615 (br), 1445, 1400, 1152, 1115, 1090, 1045, 950, and 892 cm$^{-1}$; ms: hr-fab 911.5425 (M+H+) for $C_{54}H_{75}N_2O_{10}$. The 400 MHz proton and carbon magnetic resonance data has been displayed in Tables 1 and 2.

EXAMPLE VII

Cephalostatin 2

The fraction designated Cephalostatin 2 was analyzed with the following results: UV (EtOH) 202 and 205 (10,785), 290 (13,727), 308 (sh); IR (KBr) 3430, 3055, 2975, 2930, 2880, 1710, 1655–1625 (br), 1448, 1402, 1385, 1092, 1045, and 950 cm$^{-1}$; ms: hr-fab 927.5230 (M+H+) for $C_{54}H_{75}N_2O_{11}$. The 400 MHz proton and carbon magnetic resonance data has been displayed in Tables 3 and 4.

EXAMPLE VIII

Cephalostatin 3

The fraction designated Cephalostatin 3 was analyzed with the following results: UV (EtOH) 203, 205, and 207 (8,207), 290 (12,866), 308 (sh); IR (KBr) 3430, 3050, 2967, 2928, 2872, 1707, 1645–1615 (br), 1446, 1383, 1088, 1040, 977, 952, and 935 cm$^1$; ms: hr-fab 941.5546 (M+H+) for $C_{55}H_{77}N_2O_{10}$. The 400 MHz proton and carbon magnetic resonance data has been displayed in Tables 3 and 4.

EXAMPLE IX

Cephalostatin 4

The fraction designated Cephalostatin 4 was analyzed with the following results: mp>350° C.; $[\alpha]_D$ +89° (c=0.11, $CH_3OH$); SP-HRSIMS: (glycerol—$CF_3SO_3H$) 943.5309 (M+H+)$^+$ for $C_{54}H_{75}N_2O_{12}$, calcd. 943.5243; UV (EtOH): 290 (10,500), 308 (sh) nm; IR (KBr): 3430, 2970, 2928, 2975, 1711, 1660–1600 (br), 1447, 1383, 1089, 1042, 948, and 904 cm$^{-1}$; ms=hr-Fab: The 400 mHz proton and carbon magnetic resonance data is shown in Tables 3 and 4.

EXAMPLE X $^1$H nmr assigments for cephalostatins 2, 3, 4 were determined in pyridine-$d_5$ solution. The results are reported in Table 3, below.

TABLE 3

| Carbon no. | Structure no. 2 | 3 | 4 |
|---|---|---|---|
| 1a | 3.09 (d, 16.8) | 3.09 (d, 16.7) | 3.08 (d, 17.0) |
| 1b | 2.62 | 2.62 | 2.56 |
| 4a | 2.82 | 2.82 | 2.86 |
| 4b | 2.67 | 2.67 | 2.70 |
| 5 | 1.57 | 1.57 | 1.58 |
| 6a | 1.68 | 1.68 | 1.67 |
| 6b | 1.45 | 1.45 | 1.48 |
| 7a | 1.65 | 1.65 | 1.66 |
| 7b | 1.27 | 1.27 | 1.27 |
| 8 | 2.05 | 2.06 | 2.05 |
| 9 | 0.87 (dt, 3.3, 11.5) | 0.86 (dt, 4.0, 11.8) | 0.86 (dt, 4.0, 12.0) |
| 11a | 2.03 | 2.05 | 2.05 |
| 11b | 1.76 (q, 12.0) | 1.75 (q, 12.0) | 1.76 (q, 12.0) |
| 12 | 4.05 (dd, 11.5, 4.8) | 4.05 (dd, 12.0, 5.5) | 4.06 (dd, 12.0, 5.2) |
| 15 | 5.62 (s) | 5.63 (s) | 5.64 (s) |
| 16a | 5.24 (s) | 5.23 (s) | 5.24 (s) |
| 16b | — | — | — |
| 17 | — | — | — |
| 18 | 1.33 (s, 3H) | 1.33 (s, 3H) | 1.33 (s, 3H) |
| 19 | 0.75 (s, 3H) | 0.75 (s, 3H) | 0.75 (s, 3H) |
| 20 | 2.85 | 2.85 | 2.86 |
| 21 | 1.34 (d, 7.0, 3H) | 1.35 (d, 7.0, 3H) | 1.35 (d, 7.0, 3H) |
| 23 | 4.79 (m) | 4.81 (m) | 4.80 (m) |

TABLE 3-continued

| | | | |
|---|---|---|---|
| 24a | 2.72 | 2.71 | 2.73 |
| 24b | 2.35 (t, 10.9) | 2.35 (t, 10.9) | 2.32 |
| 26a | 3.80 (d, 11.2) | 3.81 (d, 11.2) | 3.81 (d, 11.2) |
| 26b | 3.71 (d, 11.2) | 3.71 (d, 11.2) | 3.71 (d, 11.2) |
| 27 | 1.64 (s, 3H) | 1.64 (s, 3H) | 1.64 (s, 3H) |
| 28 | — | — | — |

| Carbon no. | Structure no. 2' | 3' | 4' |
|---|---|---|---|
| 1a | 3.75 (d, 17.0) | 3.78 (d, 18.0) | 3.76 (d, 17.0) |
| 1b | 2.94 | 2.95 | 2.88 |
| 4a | 3.06 (dd, 17.8, 5.3) | 3.04 (dd, 18.0, 5.0) | 3.09 |
| 4b | 2.74 | 2.75 | 2.74 |
| 5 | 2.58 | 2.58 | 2.58 |
| 6a | 1.45 | 1.47 | 1.58 |
| 6b | 1.22 | 1.22 | 1.44 |
| 7a | 2.03 | 1.98 | 1.97 |
| 7b | 1.92 | 1.95 | 1.33 |
| 8 | 2.76 | 2.75 | 2.71 |
| 9 | — | — | — |
| 11a | 3.31 (d, 14.0) | 3.35 (d, 14.0) | 3.51 (d, 14.3) |
| 11b | 2.95 | 2.95 | 3.01 (d, 14.1) |
| 12 | — | — | — |
| 15 | 5.57 (s) | 5.56 (s) | 3.38 (s) |
| 16a | 2.92 | 2.91 | 2.33 |
| 16b | 2.25 (ddd, 13.5, 8.0, 1.0) | 2.21 (ddd, 14.2, 8.0, 1.0) | 2.06 |
| 17 | 2.80 | 2.77 | 2.59 |
| 18 | 4.14 (2H) | 4.21 (2H) | 4.20 (d, 12.0) 4.31 (d, 12.0) |
| 19 | 0.97 (s, 3H) | 0.97 (s, 3H) | 1.06 (s, 3H) |
| 20 | 3.19 (dq, 6.6) | 3.19 (dq, 6.7) | 2.96 |
| 21 | 1.40 (d, 6.5, 3H) 1.27 (d, 6.8, 3H) | 1.30 (d, 6.8, 3H) | |
| 23 | 4.81 (m) | 4.35 (d, 9.7) | 4.79 (m) |
| 24a | 2.37 (dd, 12.3, 6.8) | 2.04 | 2.33 |
| 24b | 1.92 (dd, 12.0, 6.1) | — | 1.91 |
| 26a | 1.47 (s, 3H) | 1.29 (s, 3H) | 1.45 (s, 3H) |
| 26b | — | — | — |
| 27 | 1.40 (s, 3H) | 1.25 (s, 3H) | 1.40 (s, 3H) |
| 28 | — | 1.10 (d, 6.9) | — |

*(Multiplicity, J in Hz); Where no multiplicity is noted, it was not determined due to overlapping signals.

EXAMPLE XI $^{13}$C nmr assignments for cephalostatin 2, 3, 4 were determined in pyridine-$d_5$ solution. The results are reported in Table 4, below.

TABLE 4

| Carbon no. | Structure no. | | | | | |
|---|---|---|---|---|---|---|
| | 2 | 3 | 4 | 2' | 3' | 4' |
| 1 | 45.98 | 45.98 | 45.99 | 39.52 | 39.52 | 39.03 |
| 2 | 148.56* | 148.67# | 148.68 | 148.69* | 148.67# | 149.20 |
| 3 | 148.56* | 148.67# | 148.60 | 148.56* | 148.51# | 148.14 |
| 4 | 35.77 | 35.77 | 35.77 | 36.20 | 36.20 | 36.07 |
| 5 | 41.82 | 41.80 | 41.78 | 34.21 | 34.19 | 33.85 |
| 6 | 28.16 | 28.16 | 28.21 | 28.25 | 28.25 | 27.56 |
| 7 | 28.70 | 28.68 | 28.65 | 24.58 | 24.60 | 20.64 |
| 8 | 33.80 | 33.79 | 33.78 | 38.98 | 39.03 | 34.62 |
| 9 | 53.22 | 53.20 | 53.18 | 78.74 | 78.73 | 80.97 |
| 10 | 36.35 | 36.33 | 36.32 | 41.23 | 41.22 | 41.54 |
| 11 | 28.96 | 28.95 | 28.94 | 45.60 | 45.46 | 45.55 |
| 12 | 75.61 | 75.59 | 75.58 | 211.06 | 211.14 | 209.36 |
| 13 | 55.41 | 55.40 | 55.38 | 61.57 | 61.25 | 56.33 |
| 14 | 152.74 | 152.73 | 152.71 | 148.28* | 148.27# | 72.83 |
| 15 | 122.28 | 122.27 | 122.26 | 124.48 | 124.51 | 54.10 |
| 16 | 93.17 | 93.16 | 93.15 | 32.56 | 32.42 | 27.70 |
| 17 | 91.68 | 91.67 | 91.65 | 44.20 | 43.92 | 33.15 |
| 18 | 12.60 | 12.59 | 12.57 | 64.06 | 64.97 | 62.42 |
| 19 | 11.76 | 11.74 | 11.74 | 15.06 | 15.03 | 14.87 |
| 20 | 44.52 | 44.51 | 44.50 | 32.89 | 32.58 | 31.99 |
| 21 | 9.03 | 9.01 | 9.00 | 15.49 | 15.20 | 15.06 |
| 22 | 117.18 | 117.18 | 117.16 | 110.95 | 109.06 | 110.25 |
| 23 | 71.53 | 71.52 | 71.52 | 81.60 | 87.17 | 81.48 |
| 24 | 39.51 | 39.52 | 39.52 | 47.35 | 51.65 | 47.31 |
| 25 | 82.83 | 82.82 | 82.81 | 81.14 | 81.32 | 81.10 |

TABLE 4-continued

| Carbon no. | Structure no. | | | | | |
|---|---|---|---|---|---|---|
| | 2 | 3 | 4 | 2' | 3' | 4' |
| 26 | 69.30 | 69.28 | 69.28 | 29.81 | 28.02 | 29.64 |
| 27 | 26.45 | 26.43 | 26.42 | 29.53 | 23.33 | 29.32 |
| 28 | — | — | — | — | 12.71 | — |

*, # : signals can be interchanged.

EXAMPLE XII

Cephalostatin 1 was placed against the P388 lymphocytic leukemia cell line using standard National Cancer Institute ("N.C.I.") protocol with the following results:
$ED_{50} = 10^{-7} - 10^{-9}$ μg/ml
Life Extension = 31% at 40 μg/Kg host body weight

EXAMPLE XIII

Cephalostatin 2 was placed against the P388 lymphocytic leukemia cell line using standard National Cancer Institute ("N.C.I.") protocol with the following results:
$ED_{50} = 10^{-7} - 10^{-9}$ μg/ml
Life Extension = 35% at 40 μg/Kg host body weight

EXAMPLE XIV

Cephalostatin 3 was placed against the P388 lymphocytic leukemia cell line using standard National Cancer Institute ("N.C.I.") protocol with the following results:
$ED_{50} = 10^{-7} - 10^{-9}$ μg/ml
Life Extension = 30% at 40 μg/Kg host body weight

EXAMPLE XV

Cephalostatin 4 was placed against the P388 lymphocytic leukemia cell line using standard National Cancer Institute ("N.C.I.") protocol with the following results:
$ED_{50} = 5.5 \times 10^{-4}$ μg/ml
Life Extension = 25% at 100 μg/Kg host body weight From the foregoing it is readily apparent that new and useful cell growth inhibitors, pharmaceutical preparations containing such inhibitors and methods of using same have been herein described and illustrated which fulfill all of the aforestated objectives in a remarkably unexpected fashion. It is of course understood that such modifications, alterations and adaptations as will readily occur to the artisan confronted with this disclosure are intended within the spirit of the present invention which is limited only by the scope of the claims appended hereto.

Accordingly, what is claimed is:

1. A substance for inhibiting P388 lymphocytic leukemia selected from the group denominated cephalostatin 1, cephalostatin 2, cephalostatin 3, and cephalostatin 4.

2. An substance according to claim 1 having the structure:

wherein: $R_1$ is H or OH and $R_2$ is H or $CH_3$.

3. An substance according to claim 1 having the structure:

4. An substance according to claim 2 denominated cephalostatin 1 and in which $R_1=R_2=H$.

5. An substance according to claim 2 denominated cephalostatin 2 and in which $R_1=OH$ and $R_2=H$.

6. An substance according to claim 2 denominated cephalostatin 3 and in which $R_1=OH$ and $R_2=CH_3$.

7. An substance according to claim 3 denominated cephalostatin 4.

8. A pharmaceutical preparation useful in the inhibition of P388 lymphocytic leukemia comprising a pharmaceutically acceptable carrier and, as its principal active ingredient, an effective amount of an antineoplastic substance selected from the group consisting of substances denominated cephalostatin 1, cephalostatin 2, cephalostatin 3, and cephalostatin 4.

9. A pharmaceutical preparation according to claim 8 in which said substance has the structure:

wherein: $R_1$ is H or OH and $R_2$ is H or $CH_3$.

10. A pharmaceutical preparation according to claim 8 in which said substance has the structure:

11. A pharmaceutical preparation according to claim 9 in which $R_1=R_2=H$ and said substance is denominated cephalostatin 1.

12. A pharmaceutical preparation according to claim 9 in which $R_1=OH$ and $R_2=H$ and said substance is denominated cephalostatin 2.

13. A pharmaceutical preparation according to claim 9 in which $R_1=OH$ and $R_2=CH_3$ and said substance is denominated cephalostatin 3.

14. A pharmaceutical preparation according to claim 10 in which said substance is denominated cephalostatin 4.

15. A method of treating a host afflicted with lymphocytic leukemia disease comprising administering to said host a small but effective amount of a natural or synthetic substance or a pharmaceutically active non-toxic derivative thereof, said substance being selected from the group of substances denominated cephalostatin 1. cephalostatin 2, cephalostatin 3, and cephalostatin 4.

16. A method according to claim 15 in which said substance has the structure:

wherein: $R_1$ is H or OH and $R_2$ is H or $CH_3$.

17. A method according to claim 15 in which said substance has the structure:

18. A method according to claim 16 in which $R_1=R_2=H$ and said substance is denominated cephalostatin 1.

19. A method according to claim 16 in which $R_1=OH$ and $R_2=H$ and said substance is denominated cephalostatin 2.

20. A method according to claim 16 in which $R_1=OH$ and $R_2=CH_3$ and said substance is denominated cephalostatin 3.

21. A method according to claim 17 in which said substance is denominated cephalostatin 4.

22. A method according to claim 15 in which said substance is administered intravenously at a dosage level of from 0.1 up to about 20 mg per kilogram of host body weight.

23. A method according to claim 15 in which said substance is administered subcutaneously at a dosage level of from about one up to about 50 mg per kilogram of host body weight.

24. A method according to claim 15 in which said substance is administered orally at a dosage level of from about five up to about 100 mg per kilogram of host body weight.

* * * * *